(12) United States Patent
Iwasaki

(10) Patent No.: US 8,531,510 B2
(45) Date of Patent: Sep. 10, 2013

(54) ENDOSCOPE APPARATUS

(75) Inventor: Tomoki Iwasaki, Fuchu (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/587,044

(22) Filed: Aug. 16, 2012

(65) Prior Publication Data

US 2013/0038708 A1 Feb. 14, 2013

Related U.S. Application Data

(63) Continuation of application No. PCT/JP2011/061096, filed on May 13, 2011.

(30) Foreign Application Priority Data

Aug. 30, 2010 (JP) ................................. 2010-192734

(51) Int. Cl.
*G02B 7/28* (2006.01)
*G02B 23/24* (2006.01)
*G02B 23/26* (2006.01)

(52) U.S. Cl.
USPC ........................... 348/65; 348/68; 348/E7.085

(58) Field of Classification Search
None
See application file for complete search history.

(56) References Cited

U.S. PATENT DOCUMENTS

| | | | |
|---|---|---|---|
| 5,648,652 A * | 7/1997 | Sekiya et al. ............... | 250/201.7 |
| 5,749,830 A * | 5/1998 | Kaneko et al. ................. | 600/160 |
| 6,425,858 B1 * | 7/2002 | Minami ......................... | 600/168 |
| 6,956,602 B2 * | 10/2005 | Higuchi et al. .................. | 348/65 |
| 7,072,046 B2 * | 7/2006 | Xie et al. ........................ | 356/479 |
| 7,158,234 B2 * | 1/2007 | Uchiyama et al. ............. | 356/479 |
| 2008/0097151 A1 * | 4/2008 | Inoue et al. ..................... | 600/109 |
| 2010/0097454 A1 * | 4/2010 | Kubo et al. ...................... | 348/65 |
| 2010/0134606 A1 * | 6/2010 | Avni et al. ....................... | 348/65 |
| 2010/0309299 A1 * | 12/2010 | Kubo et al. ...................... | 348/68 |

FOREIGN PATENT DOCUMENTS

| | | |
|---|---|---|
| JP | 01-270842 | 10/1989 |
| JP | 06-245899 | 9/1994 |
| JP | 06-342122 | 12/1994 |
| JP | 06342122 | * 12/1994 |
| JP | 08-068721 | 3/1996 |
| JP | 08068721 | * 3/1996 |

(Continued)

OTHER PUBLICATIONS

International Search Report dated Aug. 2, 2011 issued in PCT/JP2011/061096.

*Primary Examiner* — Gims S Philippe
*Assistant Examiner* — Reza Aghevli
(74) *Attorney, Agent, or Firm* — Scully, Scott, Murphy & Presser, P.C.

(57) ABSTRACT

An endoscope apparatus having a plurality of observation modes includes: an objective optical system including a moving lens; a CCD that picks up an image of an object via the objective optical system; a contour enhancement section that performs contour enhancement of the image outputted from the CCD and outputs contour component signals; a signal value comparison section that compares a maximum value of the contour component signals and a predetermined threshold value according to the observation mode; a focusing evaluation section that determines a focusing state by determining a signal distribution of the contour component signals; and an actuator drive section that controls movement of the moving lens based on the focusing state determined by the focusing evaluation section and a result of the comparison by the signal value comparison section.

12 Claims, 12 Drawing Sheets

(56) References Cited

FOREIGN PATENT DOCUMENTS

| | | | |
|---|---|---|---|
| JP | 08-111812 | | 4/1996 |
| JP | 09-253041 | | 9/1997 |
| JP | 09253041 | * | 9/1997 |
| JP | 2000-147370 | | 5/2000 |
| JP | 2001-008097 | | 1/2001 |
| JP | 2001-154085 | | 6/2001 |
| JP | 2002-253488 | | 9/2002 |
| JP | 2002253488 | * | 9/2002 |
| JP | 2002-369794 | | 12/2002 |
| JP | 2003-061909 | | 3/2003 |
| JP | 2003061909 | * | 3/2003 |
| JP | 2004-258360 | | 9/2004 |
| JP | 2004258360 | * | 9/2004 |
| JP | 2004-294788 | | 10/2004 |
| JP | 2004294788 | * | 10/2004 |
| JP | 2006-122195 | | 5/2006 |

* cited by examiner

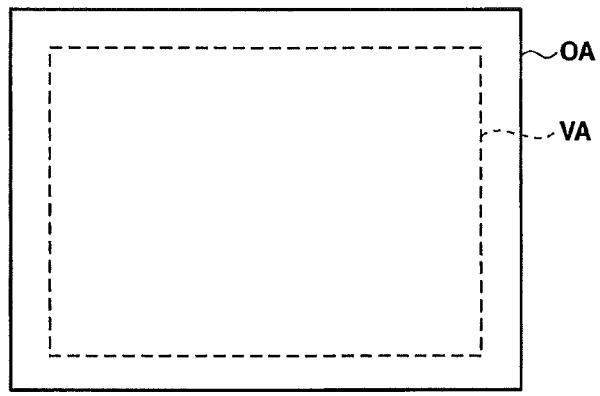

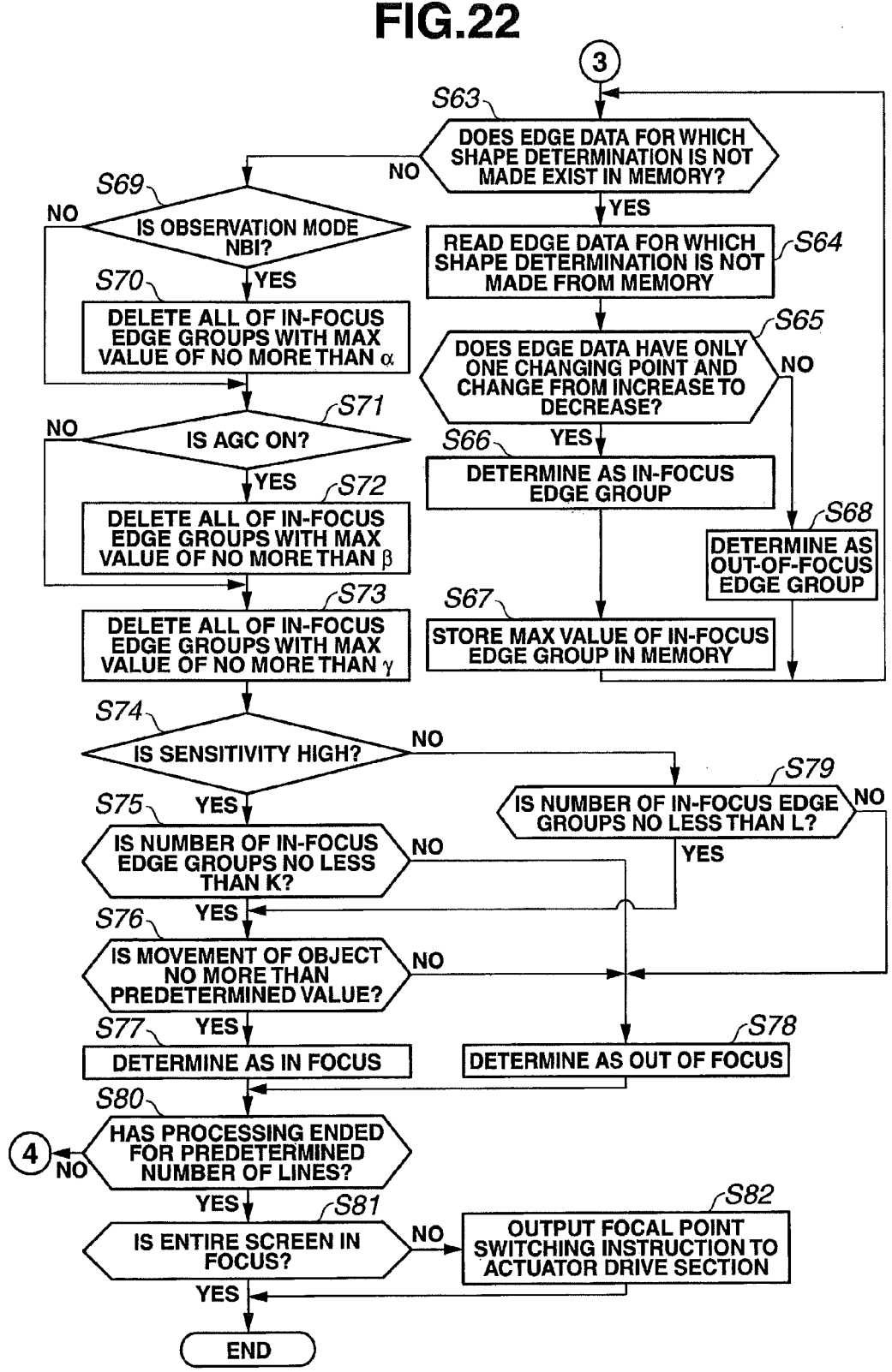

ENDOSCOPE APPARATUS

CROSS REFERENCE TO RELATED APPLICATION

This application is a continuation application of PCT/JP2011/061096 filed on May 13, 2011 and claims benefit of Japanese Application No. 2010-192734 filed in Japan on Aug. 30, 2010, the entire contents of which are incorporated herein by this reference.

BACKGROUND OF THE INVENTION

1. Field of the Invention

The present invention relates to an endoscope apparatus and specifically relates to an endoscope apparatus capable of determining a focusing state for an image.

2. Description of the Related Art

Conventionally, endoscope apparatuses have widely been used in medical and industrial fields. For example, in the medical field, a surgeon inserts an insertion portion of an endoscope into a body cavity to display an object image picked up by an image pickup device provided at a distal end of the insertion portion on a monitor, whereby the surgeon can observe a site of an object to make a diagnosis. In recent years, endoscope apparatuses having what is called an autofocusing function have been put into practical use. For example, there are endoscope apparatuses in which a focal position can be set to either a near point position or a far point position and the setting can be switched between the positions.

In general, the autofocusing function of an endoscopic image is performed based on a focusing evaluation obtained by comparison of levels of contour enhancement signals. For example, as disclosed in Japanese Patent Application Laid-Open Publication No. 2004-258360, endoscope apparatuses that perform a focusing evaluation for an image using contour enhancement processing have been proposed.

SUMMARY OF THE INVENTION

An endoscope apparatus according to an aspect of the present invention is an endoscope having a plurality of observation modes, including: an objective optical system including a moving lens; an image pickup section that picks up an image of an object via the objective optical system; a contour enhancement section that performs contour enhancement of the image outputted from the image pickup section and outputs contour component signals; a signal value comparison section that compares a maximum value of the contour component signals and a predetermined threshold value according to the observation mode; a focusing state determination section that determines a focusing state by determining a signal distribution of the contour component signals; and a drive control section that controls movement of the moving lens based on the focusing state determined by the focusing state determination section and a result of the comparison by the signal value comparison section.

BRIEF DESCRIPTION OF THE DRAWINGS

FIG. 2 is a diagram for describing an image region according to the embodiment of the present invention;

FIG. 3 is a diagram for describing a content of pixel correction processing where, e.g., a white defect exists, according to the embodiment of the present invention;

FIG. 4 is a diagram for describing the content of pixel correction processing where, e.g., the white defect exists, according to the embodiment of the present invention;

FIG. 5 is a diagram for describing the content of pixel correction processing where, e.g., the white defect exists, according to the embodiment of the present invention;

FIG. 6 is a diagram for describing the content of pixel correction processing where, e.g., the white defect exists, according to the embodiment of the present invention;

FIG. 22 is a flowchart illustrating an example of the flow of processing in the halation detection section 53, the shape detection section 54, the threshold value comparison section 55, the focal point switching instruction section 56 and the CPU I/F section 58, according to the embodiment of the present invention.

DETAILED DESCRIPTION OF THE PREFERRED EMBODIMENT

An embodiment of the present invention will be described below with reference to the drawings.
(Overall Configuration)

Figure 1:
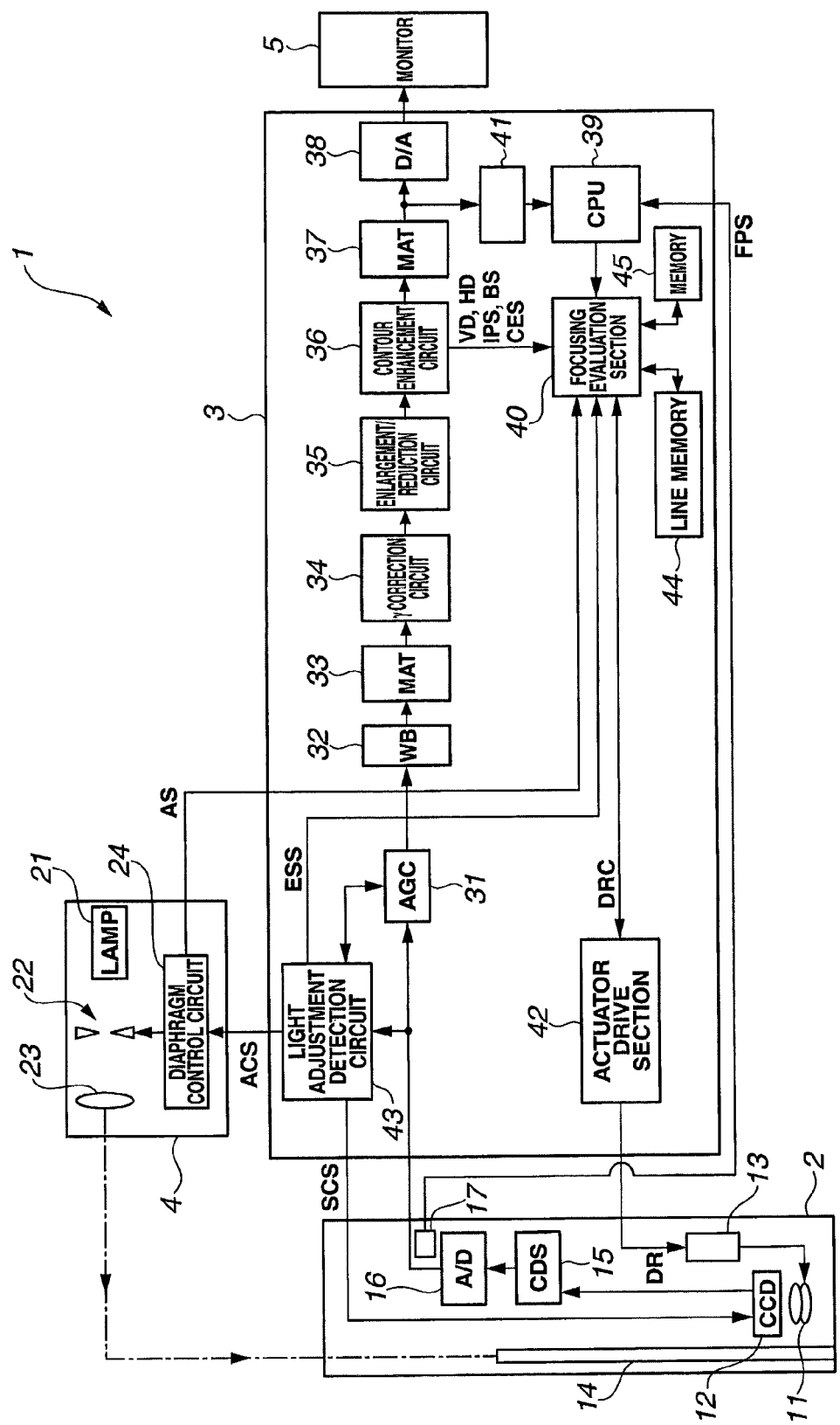
FIG. 1 is a configuration diagram illustrating a configuration of an endoscope apparatus according to an embodiment of the present invention.

First, a configuration of an endoscope apparatus according to the present embodiment will be described with reference to FIG. 1. FIG. 1 is a configuration diagram illustrating a configuration of the endoscope apparatus according to the present embodiment.

As illustrated in FIG. 1, an endoscope apparatus 1 includes an endoscope 2 including an insertion portion, a processor 3, a light source apparatus 4 and a monitor 5. The endoscope apparatus 1 has various types of observation modes for, e.g., normal observation images and narrow-band observation images, and allows setting in which mode a user observes an object.

The endoscope 2 includes an objective optical system 1 provided in a distal end portion of the insertion portion, a CCD 12 arranged so that an image pickup surface is placed at a focal position of the objective optical system 1, an actuator 13 for driving a part of lenses in the objective optical system 1 for focal point adjustment, a light guide 14 for irradiating illuminating light from the distal end portion of the insertion portion, the light guide 14 including an optical fiber bundle, a correlated double sampling circuit (hereinafter referred to as CDS circuit) 15, an analog/digital conversion circuit (hereinafter referred to as A/D conversion circuit) 16 and a ROM 17.

A distal end portion of the light guide 14 is fixed to an opening portion for illumination at the distal end portion of the insertion portion. Illuminating light from the light source apparatus 4 enters from a proximal end portion of the light guide 14, passes through the light guide 14, exits from the distal end portion of the light guide 14 and illuminates an object.

A reflected light from the object passes through the objective optical system 1 including a moving lens and forms an image on the image pickup surface of the CCD 12, which is an image pickup section. The CCD 12 photoelectrically converts the object image formed on the image pickup surface and outputs image pickup signals to the CDS circuit 15. The CDS circuit 15 performs correlated double sampling processing on the image pickup signals and outputs the resulting image pickup signals to the A/D conversion circuit 16. The A/D conversion circuit 16 converts the image pickup signals from analog signals to digital signals and outputs the resulting image pickup signals to the processor 3.

The ROM 17, which is a non-volatile memory, stores forceps position information and horizontal flip information, which will be described later. When the endoscope 2 is connected to the processor 3, e.g., the forceps position information in the ROM 17 can be read by the processor 3.

A forceps can be inserted into a channel (not illustrated) provided in the insertion portion of the endoscope 2. The forceps can be made to project from a distal end opening portion provided at the distal end portion of the insertion portion. Although a distal end portion of the projecting forceps appears in an endoscopic image picked up by the CCD 12, a position of the forceps appearing in an endoscopic image is determined in advance according to a structure of the distal end portion of the insertion portion and a positional relationship between an opening of the channel and the CCD 12. In other words, the position of the forceps appearing in the endoscopic image is determined in advance for a respective endoscope, and thus, forceps position information is stored in the ROM 17.

Furthermore, the ROM 17 also stores horizontal flip information indicating a right and left determination of an image. Among the endoscopes, there are side-viewing endoscopes in which a prism is disposed at a distal end portion of an insertion portion of the endoscope to obtain an image of an area on a side of the insertion portion. In such case, a horizontally-flipped object image is projected on the image pickup surface of the CCD 12. Accordingly, horizontal flip information such as, for example, a horizontal flip flag is stored in the ROM 17, and a CPU 39 reads the horizontal flip information, and if the horizontal flip flag indicates "1", horizontal flip processing is performed during image processing. The horizontal flip processing is performed in a later-described enlargement/reduction circuit 35 or a non-illustrated other circuit based on an instruction from the CPU 39.

The light source apparatus 4 includes a lamp 21, a diaphragm 22, a lens 23 and a diaphragm control circuit 24. Light from the lamp 21 enters the lens 23 via the diaphragm 22 controlled by the diaphragm control circuit 24. The lens 23 collects the light to the proximal end portion of the light guide 14. The collected light passes through the inside of the light guide 14 as illuminating light and exits from the distal end portion of the light guide 14. The diaphragm control circuit 24 controls the diaphragm 22 based on a diaphragm control signal ACS from the processor 3, and supplies a current diaphragm value to the processor 3 as a diaphragm value signal AS. Accordingly, the diaphragm control circuit 24 provides a diaphragm value detection section that detects a diaphragm value for adjusting a light amount of illuminating light from the light source apparatus 4.

The processor 3 includes an automatic gain control circuit (hereinafter referred to as AGC circuit) 31, a white balance circuit (hereinafter referred to as WB circuit) 32, a matrix circuit (MAT) 33, a gamma correction circuit (hereinafter referred to as γ correction circuit) 34, an enlargement/reduction circuit 35, a contour enhancement circuit 36, a matrix (MAT) circuit 37, a digital/analog conversion circuit (hereinafter referred to as D/A conversion circuit) 38, a central processing unit (hereinafter referred to as CPU) 39, a focusing evaluation section 40, a frame comparison circuit 41, an actuator drive section 42, a light adjustment detection circuit 43, a line memory 44 and a memory 45.

Image pickup signals from the A/D conversion circuit 16 in the endoscope 2 are supplied to the AGC circuit 31, subjected to gain adjustment and supplied to the white balance circuit 32. The white balance circuit 32 performs white balance adjustment of the image pickup signals. The AGC circuit 31 can be turned on/off according to a setting by a user.

The image pickup signals with its white balance corrected are supplied to the matrix circuit 33 for generating various types of images, to generate an image according to various types of observation modes such as an image according to normal observation image and an image according to narrow band observation image.

The generated image is subjected to gamma correction in the gamma correction circuit 34, further subjected to processing for enlarging and reducing the image in the enlargement/reduction circuit 35 and supplied to the contour enhancement circuit 36.

The contour enhancement circuit 36, which is a contour enhancement section, subjects the image subjected to the enlargement and reduction processing to contour enhancement processing, and supplies the image subjected to the contour enhancement processing to the matrix circuit 37. Also, the contour enhancement circuit 36 outputs later-described contour component signals CES and luminance signals BS to the focusing evaluation section 40. The contour component signals CES are signals generated for respective pixels. Accordingly, the contour enhancement circuit 36 provides a contour component signal generation section. Furthermore, the contour enhancement circuit 36 provides a luminance value detection section that detects a luminance value of each pixel in an image.

Note that in the present embodiment, the contour enhancement circuit 36 supplies a vertical drive signal VD, a horizontal drive signal HD and image position information IPS defining an effective pixel region VA to the focusing evaluation section 40 in addition to the contour component signals CES and the luminance signals BS. The contour component signals CES will be described later.

The matrix circuit 37 generates an image to be outputted to the monitor 5 and outputs the image to the D/A conversion circuit 38. The monitor 5 displays the image based on the image signal, which is an analog signal resulting from conversion in the D/A conversion circuit 38.

The CPU 39 performs overall control of the endoscope apparatus 1 and supplies various types of information to the focusing evaluation section 40 based on operation instruction signals from a non-illustrated operation panel of the processor 3 and a non-illustrated operation portion of the endoscope 2.

Furthermore, information on variation of an image between two consecutive frames is inputted from the frame comparison circuit 41 to the CPU 39. For example, when the insertion portion of the endoscope is being inserted into a body cavity, a video image obtained by the CCD 12 has fast movement, and thus, the image largely varies between frames. The frame comparison circuit 41 generates information on such variation of an image, for example, information on an amount of variation, between frames and outputs the information to the CPU 39.

The focusing evaluation section 40 performs focusing evaluation based on various types of signals from the CPU 39, the diaphragm value signal AS from the diaphragm control circuit 24, electronic shutter information ESS from the later-described light adjustment detection circuit 43, and the contour component signals CES, the luminance signals BS, the vertical drive signal VD, the horizontal drive signal HD and the image position information IPS from the contour enhancement circuit 36. As described later, the focusing evaluation section 40 provides a focusing determination section that determines a focusing state for an image by determining a signal distribution of the contour component signals CES. In the present embodiment, the focusing evaluation section 40 is a software program executed by the CPU 39. The focusing evaluation section 40 performs processing while storing necessary information in the line memory 44 and the memory 45.

The focusing evaluation section 40, which is a focusing determination section, supplies a drive control signal DRC to the actuator drive section 42, and the actuator drive section 42 outputs a drive signal DR to the actuator 13 in the endoscope 2. The actuator 13 drives the moving lens in the objective optical system 1. The actuator drive section 42 feeds a state of the actuator 13 back to the focusing evaluation section 40. The actuator drive section 42 provides a drive control section that moves the moving lens in the objective optical system 1 to a focus position based on the focusing state.

Also, the CPU 39 reads the forceps position information stored in the ROM 17 in the endoscope 2 and supplies the forceps position information to the focusing evaluation section 40.

Furthermore, the CPU 39 supplies various types of information to the focusing evaluation section 40. Example of various types of information include, e.g., observation mode information, prohibition mode information and information on various types of set values.

The frame comparison circuit 41 sequentially inputs frame information on images outputted from the matrix circuit 37, and compares two consecutive frames to detect a degree of variation of an image between the two consecutive frames. Examples of a situation when variation of an image between two consecutive frames is large include a situation when an operation to insert an insertion portion of an endoscope into a body cavity is being performed.

The frame comparison circuit 41 supplies information on variation of an image between two consecutive frames to the CPU 39.

The light adjustment detection circuit 43, to which image pickup signals from the A/D conversion circuit 16 are inputted, determines brightness of an obtained endoscopic image in its entirety. The light adjustment detection circuit 43 generates a diaphragm control signal ACS based on the brightness and supplies the diaphragm control signal ACS to the diaphragm control circuit 24, and supplies a control signal SCS for electronic shutter control for the CCD 12 to the CCD 12. Also, the light adjustment detection circuit 43 provides an electronic shutter state detection section that detects a state of an electronic shutter in the CCD 12.

Furthermore, the light adjustment detection circuit 43 generates a control signal for automatic gain control and supplies the control signal to the AGC circuit 31. The AGC circuit 31 determines a set value of a gain based on information on brightness of an entire screen from the light adjustment detection circuit 43. Note that the light adjustment detection circuit 43 receives a feedback signal of the gain value from the AGC circuit 31.

Note that if the AGC circuit 31 has a high AGC level, the endoscopic image itself becomes bright, but in contrast, noise appearing on the screen increases, resulting in a decrease in precision of focal point switching control in the later-described focusing evaluation section 40. Thus, where the AGC level is high, a low-pass filter may be provided inside the contour enhancement circuit 36 for S/N improvement by shifting a frequency band of the low-pass filter to be lower.

(Image Generation)

Here, images and processing on the images will be described.

FIG. 2 is a diagram for describing an image region. As illustrated in FIG. 2, the CCD 15 includes an effective pixel region VA in a pixel region OA defined by the vertical drive signal VD and the horizontal drive signal HD. The effective pixel region VA used for display of an endoscopic image is partially enlarged or reduced by the enlargement/reduction circuit 35, and the enlarged or reduced image is displayed on the monitor 5.

The effective pixel region VA is designated by parameters in X-Y coordinates of the pixel region OA, which are obtained from the CCD 12, and unnecessary information electrically generated in the CCD 12 (that is, an image in a non-effective pixel region) is masked.

Furthermore, in order to display an image on the monitor 5, in the case of an HDTV, it is necessary to change an enlargement factor and/or change the timing for outputting an image subjected to enlargement processing in view of an aspect ratio such as 16:9 or 4:3, and thus, the timing for outputting a mask signal for that change is also changed.

Note that if there is no unnecessary information that is electrically generated because an image outputted from the CCD 12 optically meets desired specifications, there is no need to add a mask. Furthermore, even though unnecessary information is electrically generated, there is no need to add a mask outside the display region according to the aspect ratio.

As described above, parameters for a region subject to enlargement processing are properly set according to the aspect ratio and the enlargement factor so that an endoscopic image displayed as large as possible in a display region according to the aspect ratio, whereby high-quality monitor display can be provided. In other words, the aforementioned parameters are properly set, whereby the region subject to enlargement processing can be maximized, and thus, the enlargement factor in the enlargement processing can be suppressed to be small to the possible extent, and as a result, an endoscopic image with favorable image quality can be displayed on the monitor 5.

Furthermore, white defects and vertical defects may exist in the image pickup surface of the CCD 15. Therefore, if white defects and/or vertical defects exist, pixel correction is performed by a non-illustrated correction circuit before the pixels are inputted to the matrix circuit 33 in the processor 3.

Each of FIGS. 3 to 8 is a diagram for describing the content of pixel correction processing where, e.g., a white defect exists.

FIG. 3 is a diagram for describing a case where a certain pixel is a white defect pixel, and eight pixels in the periphery of that pixel are normal pixels. In FIG. 3, a pixel value of a white defect pixel E is determined according to expression (1) below. In other words, the pixel value of the pixel E, which is a pixel to be corrected, is an average value of pixel values of the peripheral pixels A, B, C, D, F, G, H and I. Note that in the description below, A, B, C, D, E, F, G, H and I denote pixel values of the respective pixels A, B, C, D, E, F, G, H and I.

$$E=(A+B+C+D+F+G+H+I)/8 \quad \text{Expression (1)}$$

FIG. 4 is a diagram for describing a case where a white defect pixel exists at one of four corners of an image. In FIG. 4, a pixel value of a white defect pixel E at an upper left corner is determined by expression (2) below.

$$E=(3F+3H+2I)/8 \quad \text{Expression (2)}$$

FIG. 5 is a diagram for describing a case where a white defect pixel exists at a peripheral end of an image except four corners of the image. In FIG. 5, a pixel value of a white defect pixel E at an upper end is determined by expression (3) below.

$$E=(2D+2F+2H+G+I)/8 \quad \text{Expression (3)}$$

FIG. 6 is a diagram for describing a case where white defects exist also in pixels adjacent to a white defect pixel. In FIG. 6, where a pixel B that is above a pixel E, which is a white defect pixel, and a pixel A, which is one of pixels diagonally above the pixel E are white defect pixels, a pixel value of the white defect pixel E is determined according to expression (4) below.

$$E=(2C+2D+F+G+H+I)/8 \quad \text{Expression (4)}$$

Figure 7:
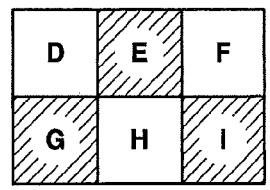
FIG. 7 is a diagram for describing the content of pixel correction processing where, e.g., the white defect exists, according to the embodiment of the present invention.

FIG. 7 is a diagram for describing another case where white defects exist also in pixels adjacent to a white defect pixel. In FIG. 7, where pixels G and I, which are both of pixels diagonally below a pixel E, which is a white defect pixel, are also white defect pixels, a pixel value of the white defect pixel E is determined according to expression (5) below.

$$E=(2D+2F+4H)/8 \quad \text{Expression (5)}$$

Figure 8:
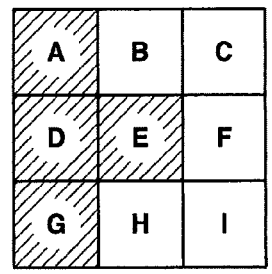
FIG. 8 is a diagram for describing the content of pixel correction processing where, e.g., the white defect exists, according to the embodiment of the present invention.

FIG. 8 is a diagram for describing a case where a vertical defect exists also in pixels adjacent to a white defect pixel. In FIG. 8, where a vertical defect exists across pixels A, D and G on the left side of a pixel E, which is a white defect pixel, a pixel value of the white defect pixel E is determined according to expression (6) below.

$$E=(2B+2F+2H+C+I)/8 \quad \text{Expression (6)}$$

Note that in the case of FIG. 3, for the pixel value of the pixel E, which is a pixel to be corrected, an average value of pixel values of a set of two pixels that sandwich the pixel E therebetween and have a smallest difference in pixel value may be determined as the pixel value of the white defect pixel E. For example, in the case of FIG. 3, in a set of A and I, a set of B and H, a set of C and G and a set of D and F, if a set with a smallest absolute value from among absolute values of respective differences, |A−I|, |B−H|, |C−G| and |D−F|, is the set of A and I, an average value of pixel values of pixels A and I may be determined as the pixel value of the white defect pixel E.

Figure 9:
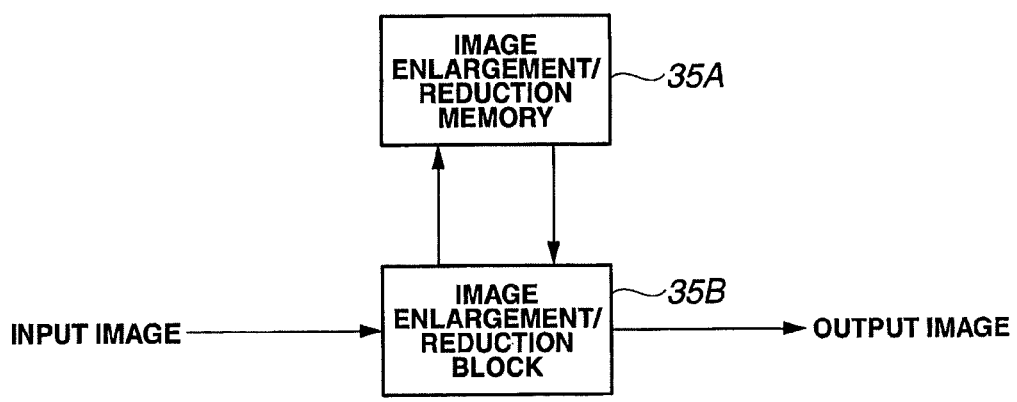
FIG. 9 is a block diagram illustrating a configuration of an enlargement/reduction circuit 35 according to the embodiment of the present invention.
Figure 10:
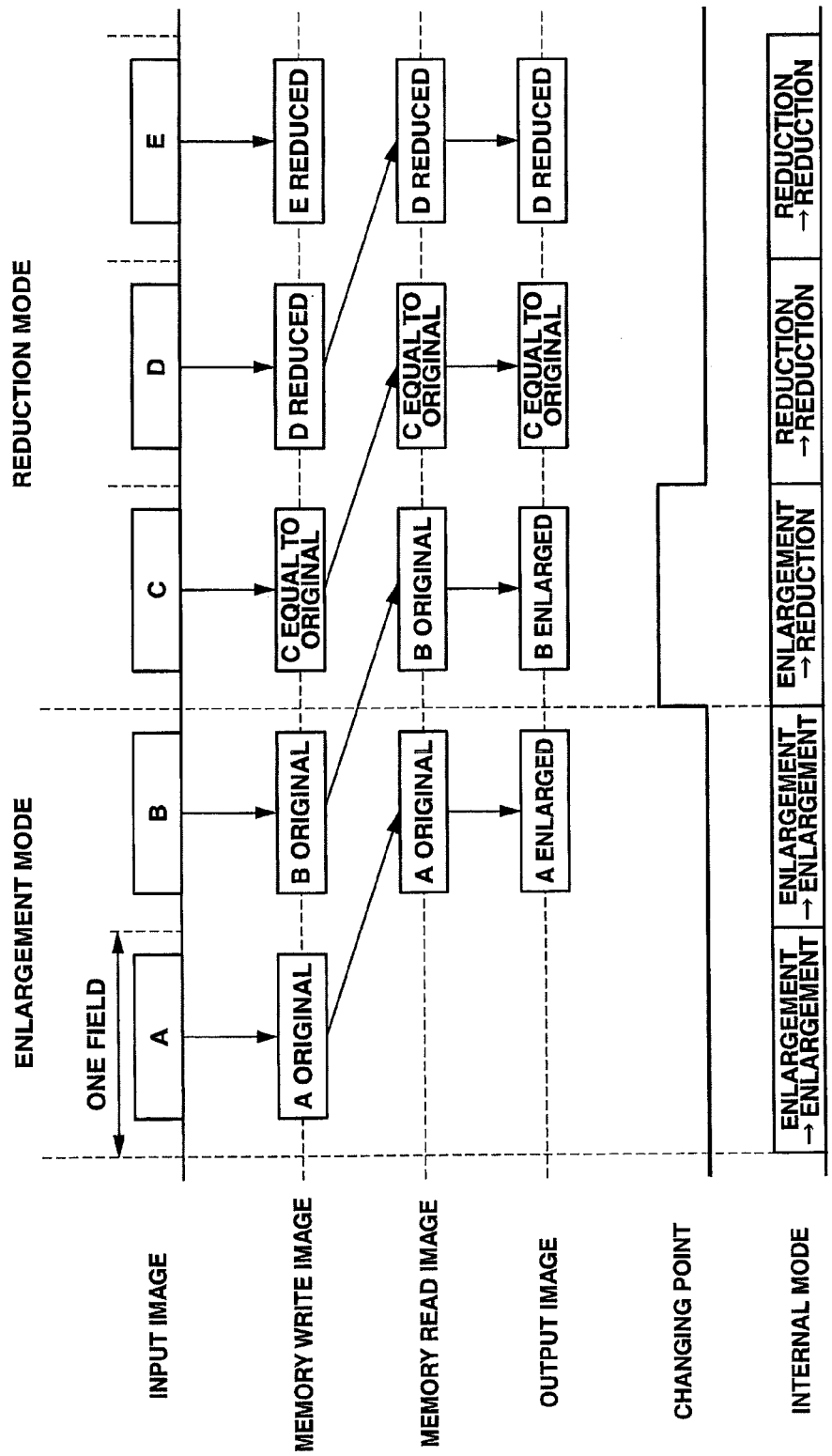
FIG. 10 is a diagram for describing change of images processed in the enlargement/reduction circuit 35, according to the embodiment of the present invention.

FIG. 9 is a block diagram illustrating a configuration of the enlargement/reduction circuit 35. FIG. 10 is a diagram for describing change of images processed in the enlargement/reduction circuit 35.

As illustrated in FIG. 9, the enlargement/reduction circuit 35 includes an image enlargement/reduction memory 35A and an image enlargement/reduction block 35B. Enlargement and reduction of images are performed using the image enlargement/reduction block 35B including a processing module used in common in both enlargement processing and reduction processing and the image enlargement/reduction memory 35A used in common. Image data is written from the image enlargement/reduction block 35B to the image enlargement/reduction memory 35A and the image data in the image enlargement/reduction memory 35A is read by the image enlargement/reduction block 35B.

An input image in an interlace method is inputted from the gamma correction circuit 34 to the image enlargement/reduction block 35B. As illustrated in FIG. 10, images in odd-numbered fields and images in even-numbered fields are alternately written to the image enlargement/reduction memory 35A as memory write images. The image data written in the image enlargement/reduction memory 35A are read by the image enlargement/reduction block 35B, subjected to enlargement processing or reduction processing and outputted as output images. Whether enlargement processing or reduction processing to be performed is determined according to whether the internal mode is an enlargement mode or a reduction mode.

Thus, upon occurrence of transition from the enlargement mode to the reduction mode, since enlargement processing and reduction processing cannot be performed simultaneously, an image such as one that cannot be recognized by a user is outputted to the monitor 5 at a changing point in the transition.

Therefore, in the enlargement/reduction circuit 35 according to the present embodiment, in order to avoid such problem, during transition from the enlargement mode to the reduction mode, an image equal to an original thereof, which provides no effect on the enlargement processing and the reduction processing, is outputted. In other words, an image displayed on the monitor 5 changes from an enlarged image to an image equal to the original and from the image equal to the original to a reduced image. As a result, the image displayed on the monitor 5 transitions while images that can be recognized by a user are displayed.

Note that although the above description has been provided in terms of an example of transition from the enlargement mode to the reduction mode, processing similar to the above may be performed for transition from the reduction mode to the enlargement mode.

(Selection of Focusing Determination Area)

Next, an area for determining, that is, evaluating a focusing state (hereinafter also referred to as focusing evaluation area) FEA in an effective pixel region VA will be described.

Figure 11:
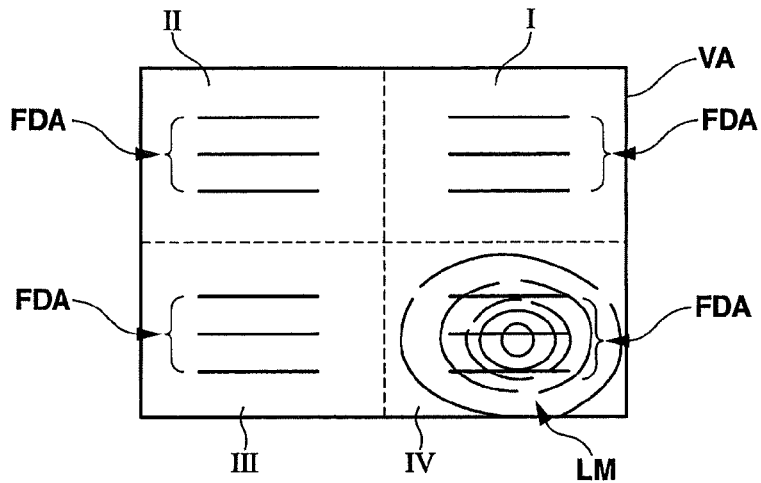
FIG. 11 illustrates an example indicating a case where a lumen LM is detected in an area IV from among four quadrants of an effective pixel region VA, according to the embodiment of the present invention.
Figure 12:
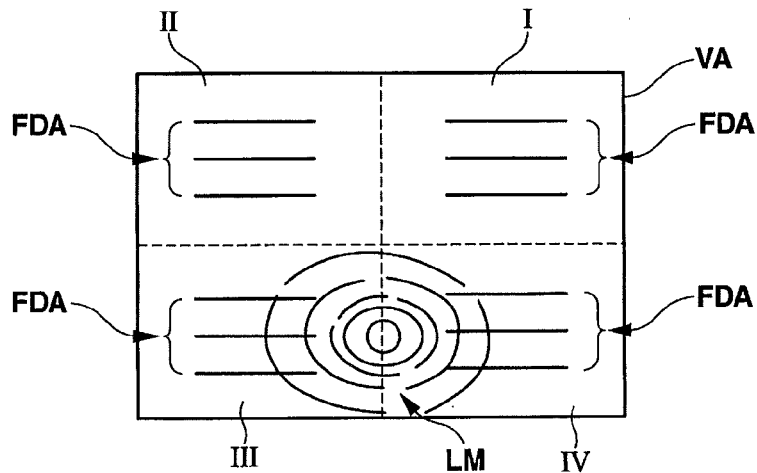
FIG. 12 illustrates an example indicating a case where the lumen LM is detected in an area III and an area IV from among four quadrants of the effective pixel region VA, according to the embodiment of the present invention.
Figure 13:
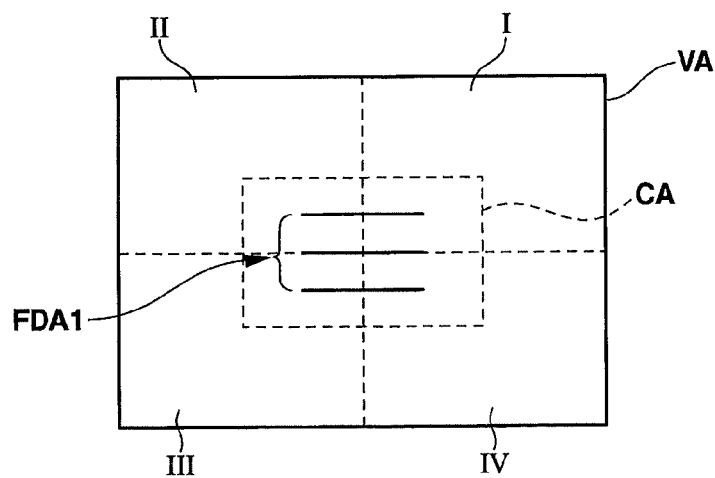
FIG. 13 illustrates an example when no lumen LM is detected in the image region VA, according to the embodiment of the present invention.

Each of FIG. 11 to FIG. 13 is a diagram for describing a focusing evaluation area FEA in an effective pixel region VA. Note that although a description will be provided here in terms of an example in which the effective pixel region VA includes areas resulting from the effective pixel region VA being divided into four, the division number may be a number other than four.

The effective pixel region VA includes four areas resulting from the effective pixel region VA being divided into four. Each area includes a focal point detection pixel group FDA for focal point detection. Also, the effective pixel region VA includes a focal point detection pixel group FDA1 for the entirety. Positions of pixels in the focal point detection pixel group FDA or FDA1 are set in advance in the image region VA. As illustrated in FIGS. 11 to 13, each of the focal point detection pixel groups FDA and FDA1 includes a plurality of, here, three linear focal point detection pixel groups.

A reason for the above is to avoid an increase in circuit size for focal point detection, which is caused when all of pixels in the respective area are used as pixels for focal point detection, and thus, pixels used for focal point detection in the respective area are determined in advance.

FIG. 11 illustrates an example indicating a case where a lumen LM is detected in a fourth quadrant IV (hereinafter also referred to as area IV) from among four quadrants in an effective pixel region VA. In the case of FIG. 11, a focal point detection pixel group FDA in a second quadrant II (hereinafter also referred to as area II) is used for focal point detection. A method for detecting a lumen LM in an effective pixel region VA will be described later.

FIG. 12 illustrates a case where a lumen LM is detected in a third quadrant III (hereinafter also referred to as area III) and the area IV from among the four quadrants in the effective pixel region VA. In the case of FIG. 12, focal point detection pixel groups FDA in a first quadrant I (hereinafter also referred to as area I) and the area II are used for focal point detection.

In other words, the above examples are examples in which the effective pixel region VA is divided into four, and when a lumen LM is detected in an endoscopic image, an area of a quadrant opposite to the quadrant where the lumen LM exists is determined as a focusing evaluation area FEA.

As described above, when a lumen LM is detected in an endoscopic image, an area where no lumen LM exists is selected as a focusing evaluation area FEA. Note that where there is a plurality of areas where no lumen LM exists, an area with a highest average luminance from among the plurality of areas may be selected as a focusing evaluation area FEA.

FIG. 13 illustrates an example in which no lumen LM is detected in the image region VA. In the case of FIG. 13, a focal point detection pixel group FDA1 in a center part CA of the image region VA is used for focal point detection.

As described above, which area is to be used as a focusing evaluation area FLA is determined in advance according to the position of the detected lumen LM and the case where no lumen LM is detected.

(Halation Pixel Cancellation)

Also, if a halation part exists in an effective pixel region VA, use of pixel values of pixels in the halation part for focal point detection results in a decrease in precision of focal point detection. This is because a halation part includes a clear edge part, which may make the focusing evaluation section 40 erroneously determine that the relevant image is in focus. Therefore, pixels in the halation part are not used for focal point detection.

Figure 14:
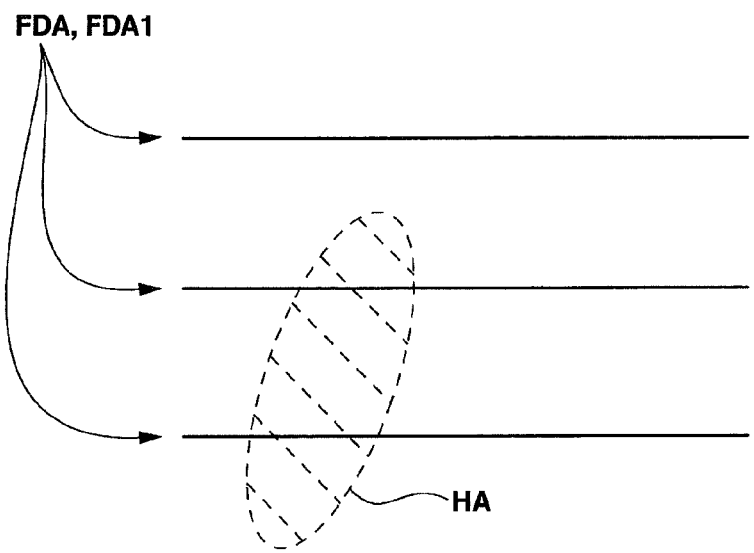
FIG. 14 is a diagram for describing a state in which a halation part exists in the effective pixel region VA and the halation part extends to a focal point detection pixel group FDA or FDA1, according to the embodiment of the present invention.

FIG. 14 is a diagram for describing a state in which a halation part exists in an effective pixel region VA and the halation part extends to a focal point detection pixel group FDA or FDA1. As illustrated in FIG. 14, where the halation part HA indicated by the dotted lines extends to a focal point detection pixel group FDA or FDA1, the pixels in the halation part HA (pixels in the shading) in the later-described focal point detection pixel group are not used for focal point detection. In other words, only pixels other than the pixels in the halation part in the focal point detection pixel group FDA or FDA1 are used for focal point detection.

Note that not only the pixels in the halation part HA but also several pixels, for example, three pixels, at the sides of the halation part HA, may be prevented from being used for focal point detection.

As described above, for focal point detection, pixels in a dark part such as a lumen and pixels in a halation part are not used for focal point detection.

(Contour Enhancement Circuit)

The contour enhancement circuit 36 generates contour component signals CES from pixel signals in the effective pixel region VA and outputs the contour component signals CES to the focusing evaluation section 40. The contour component signals CES in the present embodiment are signals containing edge component signals for respective signals, the edge component signals being obtained by making calculation from a pixel value of a pixel of interest and pixel values of a plurality of pixels (here, eight pixels) in the periphery of the pixel of interest and the pixel of interest being shifted from one to another by one pixel in a predetermined direction (here an X direction) in a two-dimensional image on an X-Y plane. In other words, the contour component signals CES are signals resulting from extracting only edge components, which are contour signals, from video signals the signals being obtained by calculating edge components for the respective pixels in the effective pixel region VA.

Figure 15:
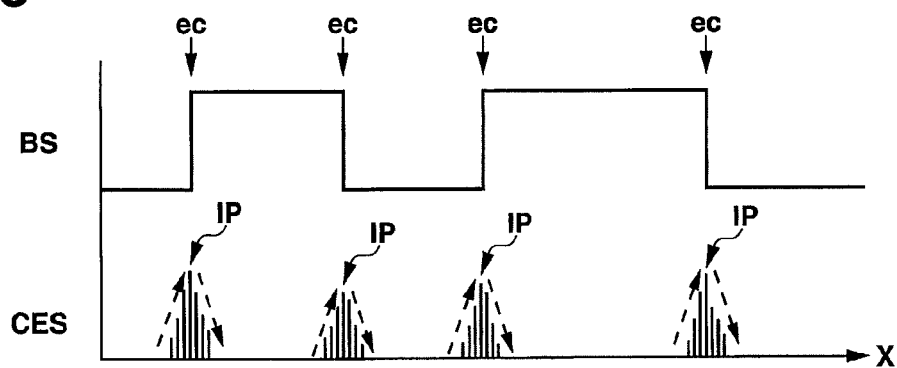
FIG. 15 is a schematic diagram for describing contour component signals CES at edge parts of an image, according to the embodiment of the present invention.

FIG. 15 is a schematic diagram for describing contour component signals CES in edge parts in an image. The contour enhancement circuit 36 calculates edge components for respective pixels of interest while shifting the pixel of interest from one to another by one pixel in the X direction for each line in an effective pixel region VA, and outputs the edge components as contour component signals CES. In other words, the contour component signals CES contain edge component values having positive values calculated for the respective pixels in the effective pixel region VA. The edge component values are values resulting from structure enhancement, and thus are large in edge parts in an image, which have clear differences in luminance value.

As illustrated in FIG. 15, in the case of an image that has large differences between values of luminance signals BS and thus is in focus, the edge component value has the characteristic of becoming the largest at an inflection point IP in the vicinity of a center ec of each edge part having a clear difference in luminance value and gradually becoming smaller away from the inflection point IP in the vicinity of the center ec. In other words, the edge component value is a value that monotonically increases and monotonically decreases before and after the inflection point IP in the vicinity of the center ec of the edge part having a clear difference in luminance value. When values of edge components are plotted by arranging the values in the X direction, the contour component signals CES are indicated by a bar chart including triangular shapes. If a plurality of edge parts having a clear difference in luminance value exist in a certain line in the effective pixel region VA, a plurality of the triangles exist in the line. In a region with no edge part, no contour component signals CES are outputted.

On the other hand, in the case of an image having no clear difference in luminance value, data of such contour component signals CES as illustrated in FIG. 15 are not obtained.

Figure 16:
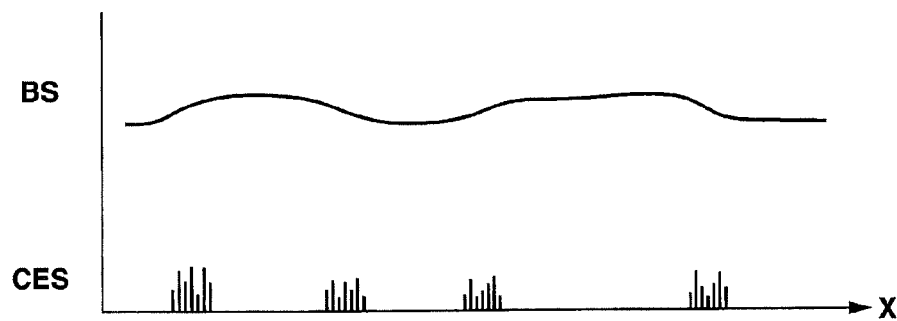
FIG. 16 is a diagram for describing contour component signals CES generated where no clear edge parts exist in the effective pixel region VA, according to the embodiment of the present invention.

FIG. 16 is a diagram for describing contour component signals CES generated where no clear edge parts exist in the effective pixel region VA.

As illustrated in FIG. 16, where there are no large differences in value of luminance signal BS and thus no clear edge parts exist, a plurality of data in the contour component signals CES in each edge part is not data in a monotonic increase and a monotonic decrease such as data having values gradually increasing toward a center part of the edge and after one inflation point at an intermediate point, gradually decreasing like that illustrated in FIG. 15. Where there are no clear edge parts in the effective pixel region VA, that is, in the case of a blurred image, the contour component signals CES for the respective pixels in the edge parts do not exhibit triangular shapes such as illustrated in FIG. 15.

As described later, if a plurality of contour component signals CES generated by making calculation from pixels while the pixels are shifted from one to another by one pixel in a predetermined direction in an image has a predetermined distribution, it is determined that the image is in focus. Then, the predetermined distribution includes a plurality of signal parts in a monotonic increase and a plurality of signal parts in a monotonic decrease following the plurality of signal parts in a monotonic increase when a plurality of contour component signals CES are generated for respective pixels in the predetermined direction and outputted, and one plurality of signal parts in a monotonic increase and one plurality of signal parts in a monotonic decrease are included in the predetermined distribution.

Note that although at an inflection point between a monotonic increase and a monotonic decrease, the contour component signal CES has a maximum value, there may be not only one contour component signal CES but two or more contour component signals CES having a maximum value, for example, there may be two or three consecutive contour component signals CES having a maximum value. Note that the below description will be provided in terms of a case where there is only one contour component signal CES having a maximum value.

(Configuration of Focusing Evaluation Section)

Figure 17:
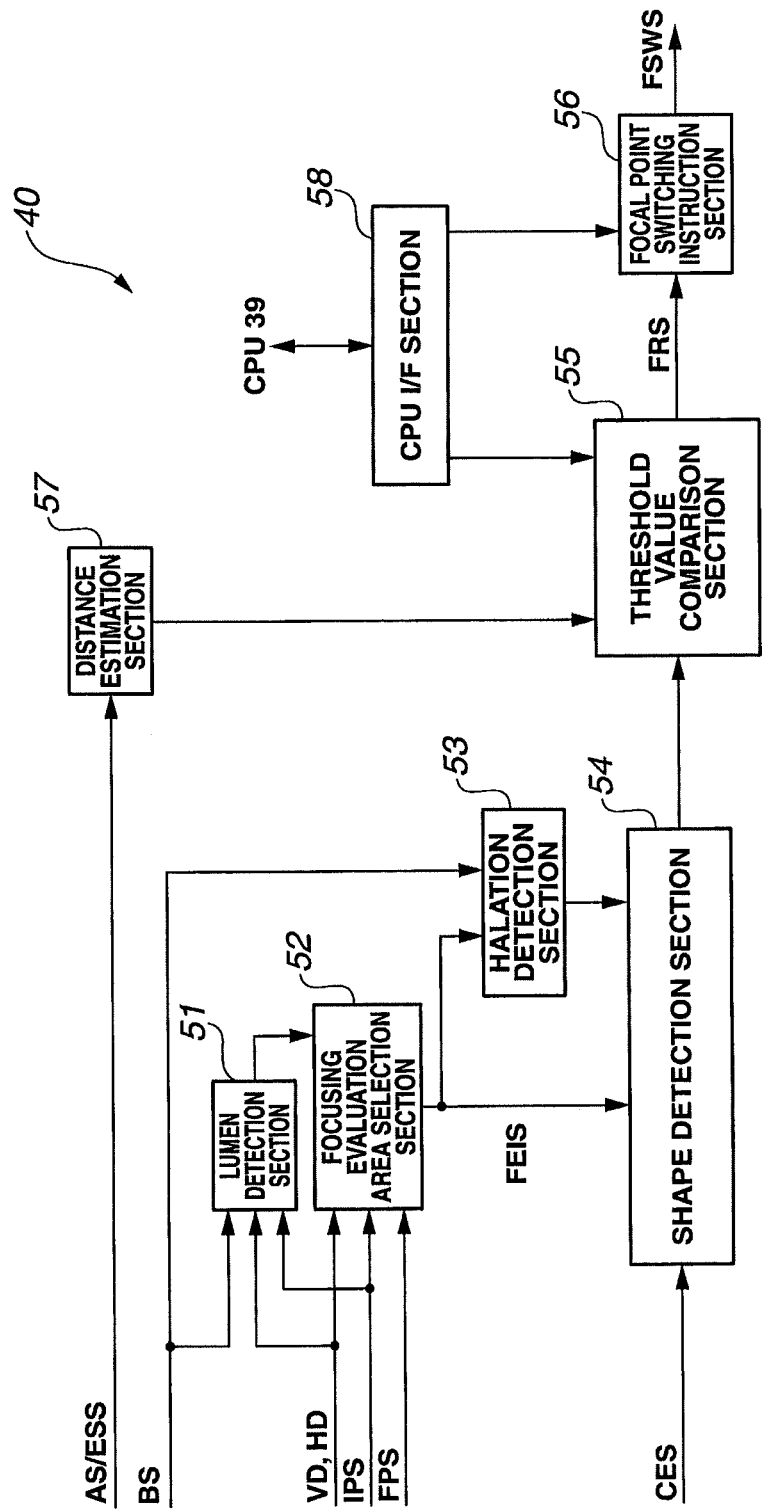
FIG. 17 is a block diagram illustrating a configuration of a focusing evaluation section 40 according to the embodiment of the present invention.

FIG. 17 is a block diagram illustrating a configuration of the focusing evaluation section 40. In the present embodiment, as described above, the focusing evaluation section 40 is a processing section provided by a software program executed by the CPU 39.

The focusing evaluation section 40 includes a lumen detection section 51, a focusing evaluation area selection section 52, a halation detection section 53, a shape detection section 54, a threshold value comparison section 55, a focal point switching instruction section 56, a distance estimation section 57, and a CPU interface section (hereinafter referred to as CPU I/F) 58.

The lumen detection section 51 is a processing section that detects existence or non-existence of a lumen in an image. The luminance signals BS from the contour enhancement circuit 36, the vertical drive signal VD and the horizontal drive signal HD from the CCD 12 and the image position information IPS defining the effective pixel region VA are inputted to the lumen detection section 51.

The lumen detection section 51 detects a pixel whose luminance value is no more than a predetermined threshold value, that is, a pixel of a dark part, and detects a position of a region of the detected dark part pixel as a position of a lumen LM. For example, if there are pixels having no more than a predetermined threshold value of brightness corresponding to an area of no less than a predetermined size, the lumen detection section 51 determines a position of the part having that area as a lumen position. Accordingly, the lumen detection section 51 detects the lumen LM from the detected luminance values.

Then, as illustrated in FIG. 11 or 12, the lumen detection section 51 outputs information on a position, that is, information on a quadrant where the lumen LM is detected.

The focusing evaluation area selection section 52 is a processing section that selects an area used for focusing evaluation in the effective pixel region VA and outputs a focusing evaluation area instruction signal FEIS. The vertical drive signal VD and the horizontal drive signal HD from the CCD 12 and the image position information IPS defining the effective pixel region VA and forceps position information FPS are inputted to the focusing evaluation area selection section 52.

In the case of FIG. 11, since the lumen LM is detected in the quadrant IV, for example, the focusing evaluation area selection section 52 outputs a focusing evaluation area instruction signal FEIS for selecting the area II as a focusing evaluation area FEA. Likewise, in the case of FIG. 12, since the lumen LM is detected in the area III and the area IV, for example, the focusing evaluation area selection section 52 selects two areas, the area I and the area II, as focusing evaluation areas FEA and outputs a focusing evaluation area instruction signal FEIS in the focusing evaluation areas FEA.

Furthermore, in the case of FIG. 13, since no lumen LM is detected in the effective pixel region VA, the focusing evaluation area selection section 52 selects the area CA in the center part as a focusing evaluation area FEA and outputs a focusing evaluation area instruction signal FEIS.

The forceps position information FPS is information on a position where a forceps appears in an image.

The halation detection section 53 is a processing section for detecting a halation part in the effective pixel region VA. The luminance signals BS, and the focusing evaluation area instruction signal FEIS from the focusing evaluation area selection section 52 are inputted to the halation detection section 53. The halation detection section 53 detects existence or non-existence of a halation in the selected focusing evaluation area FEA, and outputs information on existence or non-existence of a halation and information on positions of pixels of the halation. Note that existence or non-existence of a halation can be determined according to whether or not a pixel value of the pixel is a pixel value that is no less than a predetermined threshold value.

The shape detection section 54 is a processing section that performs shape detection processing based on the contour component signals CEA from the contour enhancement circuit 36, the focusing evaluation area instruction signal FEIS, and the information from the halation detection section 53. The content of processing in the shape detection section 54 will be described later.

The threshold value comparison section 55 is a processing section that compares the contour component signals CES exhibiting a triangular shape, outputted from the shape detection section 54, and a predetermined threshold value and outputs a focusing evaluation result signal FRS.

For example, the threshold value comparison section 55 determines whether or not a value of an inflection point IP (that is, a maximum value) of the contour component signals CES exhibiting a triangular shape, outputted from the shape detection section 54, is that of a signal having no less than a predetermined signal level threshold value, and remove contour component signals CES having a value of less than the predetermined signal level threshold value as noise signals and use only contour component signals CES other than noise signals for focusing evaluation.

Furthermore, the threshold value comparison section 55 outputs a focusing evaluation result signal FRS indicating that the relevant image is in focus according to whether or not no less than a predetermined threshold number of groups of contour component signals CES having triangular shapes are detected in each linear focal point detection pixel group and whether or not no less than a predetermined threshold number of lines having no less than the predetermined threshold number of triangular shapes are included in the plurality of lines.

For example, if a focusing evaluation area FEA includes two or more lines each including a linear focal point detection pixel group from which no less than three groups of contour component signals CES having triangular shapes are detected, the threshold value comparison section 55 outputs a focusing evaluation result signal FRS indicating that the entire screen is in focus, and if the focusing evaluation area FEA includes no more than one such line, the threshold value comparison section 55 outputs a focusing evaluation result signal FRS indicating that the entire screen is out of focus.

Note that the respective threshold values, that is, the signal level threshold value, the threshold number of groups and the threshold number of lines can be changed, and as described later, can be changed by a user via the CPU I/F 58.

The focal point switching instruction section 56 outputs a focal point switching signal FSWS for switching a focal position, based on the inputted focusing evaluation result signal FRS. For example, if the focusing evaluation result signal FRS indicates that the screen is in focus, the focal point switching instruction section 56 does not output the focal point switching signal FSWS, while if the focusing evaluation result signal FRS indicates that the screen is out of focus, the focal point switching instruction section 56 outputs the focal point switching signal FSWS. Where an endoscope has two phases of focal points, for example, where there are only two focal positions, a near point position and a far point position, if the screen is out of focus, the focal point switching instruction section 56 outputs a switching signal FSWS for switching the objective optical system 1 so that the focal point is switched to the other focal position.

The distance estimation section 57 is a processing section that performs processing for estimating a distance between a distal end portion of the endoscope and an object. The distance estimation section 57 is used to prevent the switched focal position from being a position where the screen is out of focus. That is, the distance estimation section 57 performs processing for estimating the distance to the object for prevention of malfunction of focal point switching control.

For example, where the endoscope has two focal positions, a near point focal position and a far point focal position, switching of the focal position from the far point position to the near point position is performed when the distance to the object is extremely short. Accordingly, where switching of the focal position from the far point position to the near point position is determined to be necessary for any reason when the distance to the object is long, if the distance to the object is no less than a predetermined distance, in order to prevent switching of the focal position from the far point position to the near point position, the distance estimation section 57 estimates whether or not the distance to the object is no less than the predetermined distance, and outputs a predetermined signal to the threshold value comparison section 55.

The distance estimation section 57 does not directly measure the distance from the distal end portion of the endoscope to the object but estimates whether or not the distance to the object is no less than the predetermined distance based on an amount of light emitted from the light source apparatus 4 (that is, the diaphragm value signal AS) or the electronic shutter information (ESS). In other words, the distance estimation section 57 estimates the distance to the object based on at least one of the state of the electronic shutter and the diaphragm value.

The amount of light emitted from the light source apparatus 4 is correlated with the diaphragm value of the diaphragm 22. If the distance to the object is short, the necessary amount of light is small and thus, an aperture of the diaphragm 22 is narrowed. Accordingly, if the aperture of the diaphragm indicated by the diaphragm value signal AS from the diaphragm control circuit 24 is no more than a predetermined value, the distance estimation section 57 determines that the distance to the object is no less than the predetermined distance and outputs the predetermined signal.

Also, the electronic shutter information ESS is correlated with the distance to the object. If the distance to the object is short, the amount of light projected on the object is large and thus a shutter speed of the electronic shutter becomes high. Accordingly, the shutter speed is no more than a predetermined speed value, the distance estimation section 57 determines that the distance to the object is no less than the predetermined distance, and outputs the predetermined signal.

Accordingly, when the focal position is the far point position, if the distance estimation section 57 estimates that the distance to the object is no less than the predetermined distance, the threshold value comparison section 55 prohibits an output of a focusing evaluation result signal FRS indicating whether or not the screen is in focus.

Note that, conversely, when the focal position is the far point position, only if the distance estimation section 57 estimates that the distance to the object is no more than the predetermined distance, the threshold value comparison section 55 may permit an output of a focusing evaluation result signal FRS indicating whether or not the screen is in focus.

Furthermore, even when the focal position is the near point position, if the distance to the object is such a short distance exceeding a limit of the field of depth of the objective optical system 1, the threshold value comparison section 55 also prohibits an output of a focusing evaluation result signal FRS indicating whether or not the screen is in focus. This is because where the distance to the object is too short, the screen cannot be in focus.

Accordingly, the threshold value comparison section 55 controls driving and stoppage of the moving lens based on the estimated distance. The CPU I/F 58 is a processing section that supplies control signals or control information supplied from the CPU 39 to predetermined processing sections.

Upon an input of a sensitivity value, observation mode information, an AGC level from the CPU 39, the CPU I/F 58 supplies these pieces of information to the threshold value comparison section 55. The threshold value comparison section 55 changes the respective threshold values described above according to these pieces of information. The set sensitivity value is, for example, a set value for the signal level threshold value, and as described later, change of the set sensitivity value results in change in number of contour component signals CES detected.

Also, the observation mode information is, for example, information indicating whether or not the observation mode is any of a normal-light observation mode, a narrow band observation mode and a fluorescence observation mode, and in the threshold value comparison section 55, a signal level threshold value according to the observation mode is selected and set.

Furthermore, the AGC level is a level set according to the state of noise of the image, and change of the AGC level results in change of the signal level threshold value.

Also, upon an input of prohibition mode information from the CPU 39, the CPU I/F 58 supplies the prohibition mode information to the focal point switching instruction section 56. Here, prohibition mode information is information indicating a prohibition mode for prohibiting an output from the focal point switching instruction section 56 during an operation for inserting the insertion portion of the endoscope into the subject.

During an operation for inserting the insertion portion of the endoscope into the subject, the distance between the distal end portion of the insertion portion of the endoscope and the subject becomes short and long, i.e., frequently changes. A user does not observe the subject while changing the focal length during the operation for inserting the insertion portion of the endoscope into the subject. Accordingly, in order to prevent a switching signal FSWS from being outputted from the focusing evaluation section 40 during an operation for inserting the insertion portion of the endoscope into the subject, when the CPU 39 determines that there is a change equal to or exceeding a predetermined threshold value between images of two consecutive frames, based on a comparison result signal from the frame comparison circuit 41, the CPU 39 outputs information indicating the prohibition mode to the focusing evaluation section 40.

(Operation)

Next, the flow of processing in the focusing evaluation section 40 will be described. As described above, the respective functions of the focusing evaluation section 40 are performed by the program executed by the CPU 39.

First, processing in the lumen detection section 51 and the focusing evaluation area selection section 52 in the focusing evaluation section 40 will be described.

Figure 18:
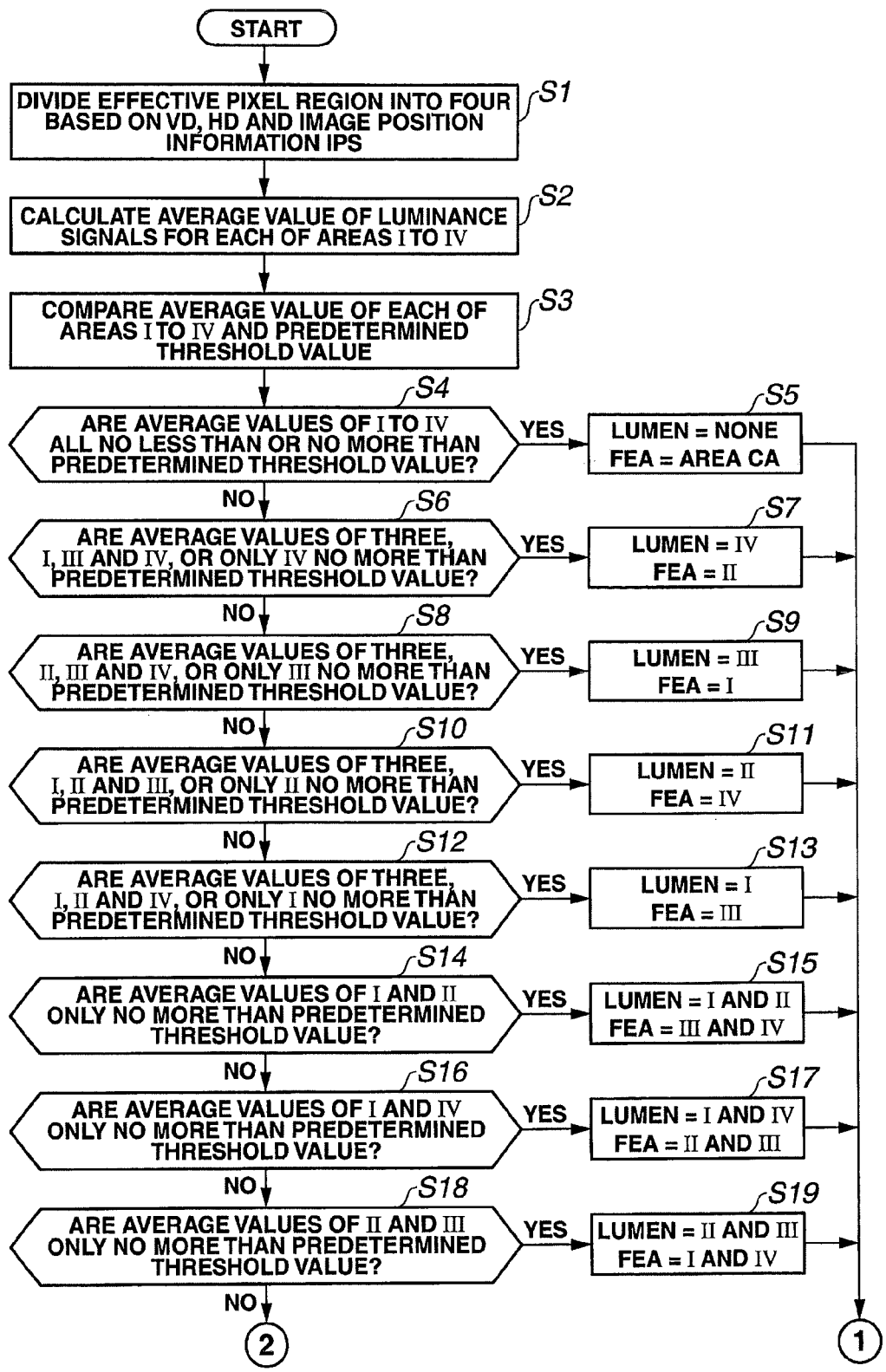
FIG. 18 is a flowchart illustrating an example of a flow of processing in a lumen detection section 51 and a focusing evaluation area selection section 52, according to the embodiment of the present invention.
Figure 19:
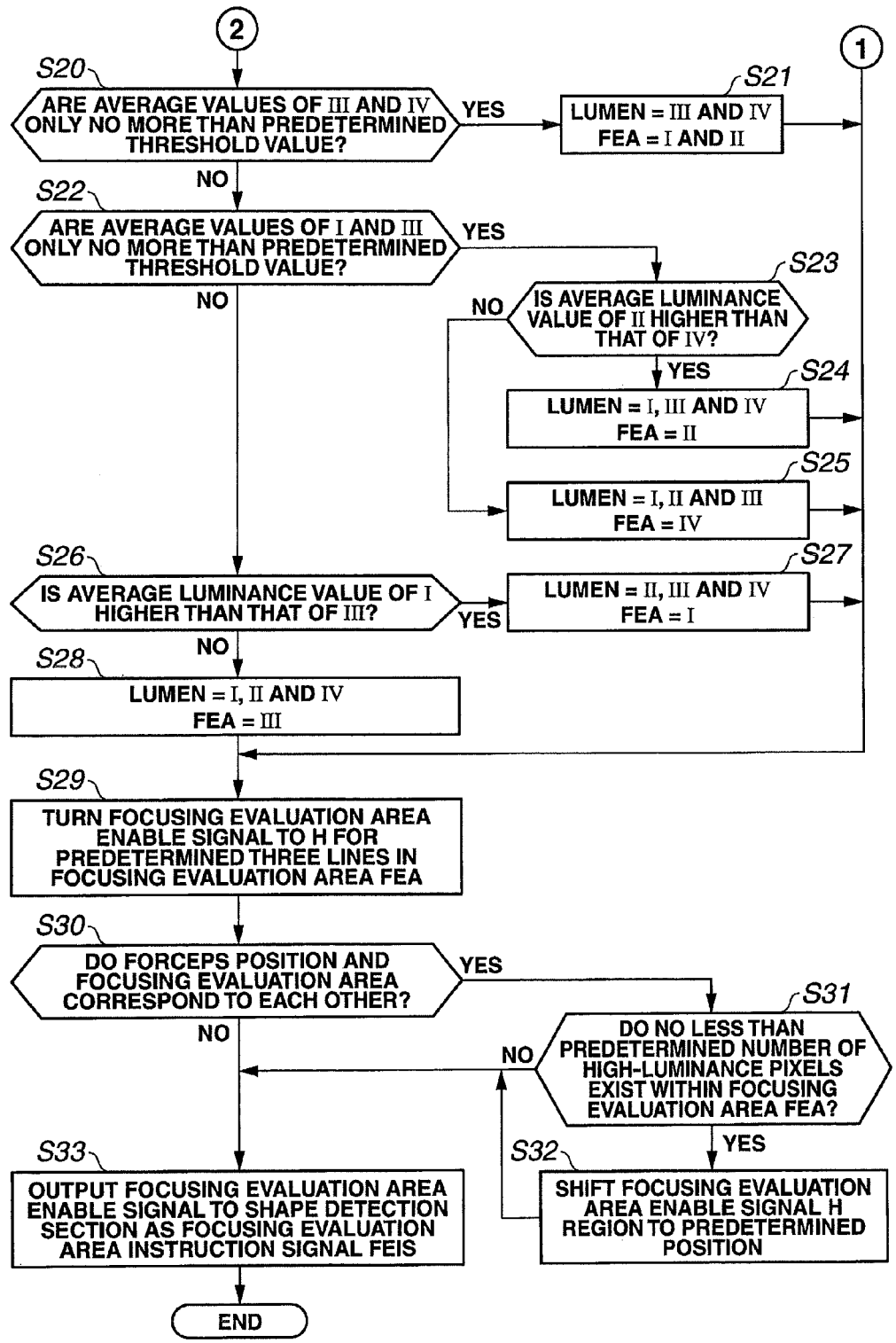
FIG. 19 is a flowchart illustrating an example of the flow of processing in the lumen detection section 51 and the focusing evaluation area selection section 52, according to the embodiment of the present invention.

FIGS. 18 and 19 are flowcharts illustrating an example of the flow of processing in the lumen detection section 51 and the focusing evaluation area selection section 52.

First, the CPU 39 divides an effective pixel region VA into four areas I, II, III and IV based on the vertical drive signal VD, the horizontal drive signal HD and information in the image position information IPS (step (hereinafter abbreviated as S) 1).

Next, the CPU 39 calculates an average value of the luminance signals BS for each of the areas I to IV (S2), and compares each of the average values for the areas I to IV and a predetermined threshold value THd (S3).

The CPU 39 determines whether or not the average values of the areas I, II, II and IV are all no less than the threshold value THd or whether or not no more than the threshold value THd (S4), and if the average values are all no less than the threshold value THd or no more than the threshold value THd (S4: YES), the CPU 39 determines that no lumen exists, and selects the area CA in the center part as a focusing evaluation area FEA (S5).

In the case of NO in S4, the CPU 39 determines whether or not the average values of the areas I, III and IV are all no more than the threshold value THd or whether or not only the average value of the area IV is no more than the threshold value THd (S6).

If the average values of the areas I, III and IV are all no more than the threshold value THd or if only the average value of the area IV is no more than the threshold value THd (S6: YES), the CPU 39 determines that a lumen exists in the area IV and selects the area II as a focusing evaluation area FEA (S7).

In the case of NO in S6, the CPU 39 determines whether or not the average values of the areas II, III and IV are all no more than the threshold value THd or whether or not only the average value of the area III is no more than the threshold value THd (S8).

If the average values of the areas II, III and IV are all no more than the threshold value THd or if only the average value of the area III is no more than the threshold value THd (S8: YES), the CPU 39 determines that a lumen exists in the area III and selects the area I as a focusing evaluation area FEA (S9).

In the case of NO in S8, the CPU 39 determines whether or not the average values of the areas I, II and III are all no more than the threshold value THd or whether or not only the average value of the area II is no more than the threshold value THd (S10).

If the average values of the areas I, II and III are all no more than the threshold value THd or if only the average value of the area II is no more than the threshold value THd (S10: YES), the CPU 39 determines that a lumen exists in the area II, and selects the area IV as a focusing evaluation area FEA (S11).

In the case of NO in S10, the CPU 39 determines whether or not the average values of the areas I, II and IV are all no more than the threshold value THd or whether or not only the average value of the area I is no more than the threshold value THd (S12).

If the average values of the areas I, II and IV are all no more than the threshold value THd or if only the average value of the area I is no more than the threshold value THd (S12:YES), the CPU 39 determines that a lumen exists in the area I and selects the area III as a focusing evaluation area FEA (S13).

In the case of NO in S12, the CPU 39 determines whether or not only the average values of two areas, the areas I and II, are no more than the threshold value THd (S14).

If only the average values of two areas, the areas I and II, are no more than the threshold value THd (S14: YES), the CPU 39 determines that a lumen exists in the areas I and II, and selects the areas III and IV as focusing evaluation areas FEA (S15).

In the case of NO in S14, the CPU 39 determines whether or not only the average values of two areas, the areas I and IV, are no more than the threshold value THd (S16).

If only the average values of two areas, the areas I and IV, are no more than the threshold value THd (S16: YES), the CPU 39 determines that a lumen exists in the areas I and IV, and selects the areas II and III as focusing evaluation areas FEA (S17).

In the case of NO in S16, the CPU 39 determines whether or not only the average values of two areas, the areas II and III, are no more than the threshold value THd (S18).

If only the average values of two areas, the areas II and III, are no more than the threshold value THd (S18: YES), the CPU 39 determines that a lumen exists in the areas II and III, and selects the areas I and IV as focusing evaluation areas FEA (S19).

In the case of NO in S18, the CPU 39 determines whether or not only the average values of two areas, the areas III and IV, are no more than the threshold value THd (S20).

If only the average values of two areas, the areas III and IV, are no more than the threshold value THd (S20: YES), the CPU 39 determines that a lumen exists in the areas III and IV, and selects the areas I and II as focusing evaluation areas FEA (S21).

In the case of NO in S20, the CPU 39 determines whether or not only the average values of two areas, the areas I and III, are no more than the threshold value THd (S22).

If only the average values of two areas, the areas I and III, are no more than the threshold value THd (S22: YES), the CPU 39 determines whether or not an average luminance value of the area II is higher than that of the area IV (S23).

If the average luminance value of the area II is higher than that of the area IV (S23: YES), the CPU 39 determines that a lumen exists in the areas I, III and IV, and selects the area II as a focusing evaluation area FEA (S24).

In the case of NO in S23, the CPU 39 determines that a lumen exists in the areas I, II and III, and determines the area IV as a focusing evaluation area FEA (S25).

If only the average values of the areas II and IV are no more than the threshold value THd (S22: NO), the CPU 39 determines whether or not an average luminance value of the area I is higher than that of the area III (S26).

If the average luminance value of the area I is higher than that of the area III (S26: YES), the CPU 39 determines that a lumen exists in the areas II, III and IV, and selects the area I as a focusing evaluation area FEA (S27).

In the case of NO in S26, the CPU 39 determines that a lumen exists in the areas I, II and IV, and selects the area III as a focusing evaluation area FEA (S28).

As described above, an image is divided into a plurality of areas and from among the plurality of areas, an area other than an area determined as including a lumen based on information on the position of the lumen is set as a focusing evaluation area (that is, focusing determination area) in the image for determining a focusing state.

As a result of the processing in S5, S7, S9, S11, S13, S15, S17, S19, S21, S24, S25, S27 and S28, the focusing evaluation area FEA is determined. Accordingly, after the processing, the CPU 39 turns focusing evaluation area enable signals to HIGH (hereinafter referred to as H), the focusing evaluation area enable signals corresponding to all of pixel positions in a focal point detection pixel group FDA or FDA1 including three lines in the effective pixel region VA (S29). In other words, while focusing evaluation area enable signals are set corresponding to positions of respective pixels in the effective pixel region VA, the focusing evaluation area enable signals for positions of pixels in the focal point detection pixel group FDA or FDA1 are set to H. Note that since two areas are selected as focusing evaluation areas FEA in S15, S17, S19 and S21, in such cases, the focusing evaluation area enable signals corresponding to positions of pixels in the focal point detection pixel groups FDA including six lines are turned to H.

Next, the CPU 39 determines whether or not an area including a forceps position and the focusing evaluation area FEA correspond to each other based on the forceps position information FPS (S30). The ROM 17 and S30 provide a forceps position detection section that detects a position of a forceps in an image picked up by the CCD 12.

If an area including a forceps position and the focusing evaluation area FEA correspond to each other (S30: YES), the CPU 39 determines whether or not no less than a predetermined number of high-luminance pixels exist in the focusing evaluation area FEA (S31). In the case of YES in S31, that is, if no less than the predetermined number of high-luminance pixels exist, an image of the forceps projecting from the distal end portion of the endoscope is included in the image.

Accordingly, in the case of YES in S31, since the position of the forceps appearing in the image is determined in advance, the CPU 39 shifts a position of a focusing evaluation area enable signal H region to a predetermined position (S32).

Figure 20:
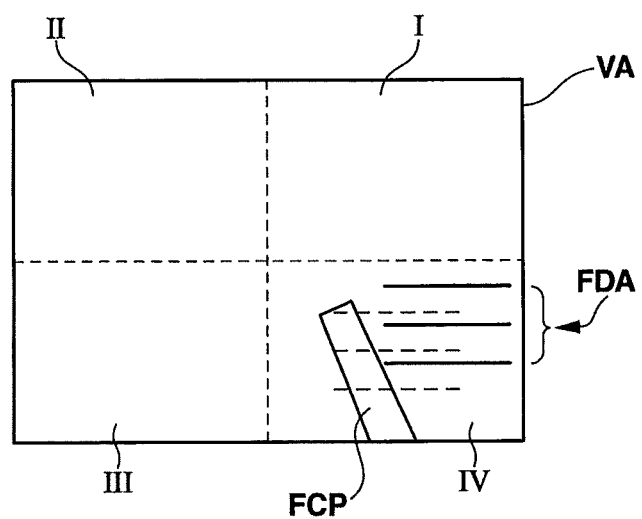
FIG. 20 is a diagram for describing a shift of a focusing evaluation area enable signal H region corresponding to positions of pixels in a focal point detection pixel group FDA, according to the embodiment of the present invention.

FIG. 20 is a diagram for describing a shift of a position of a focusing evaluation area enable signal H region corresponding to positions of pixels in a focal point detection pixel group FDA. As illustrated in FIG. 20, when the focusing evaluation area FEA is set to the area IV, a forceps FCP may appear in the area IV on the image. Thus, a position of a focusing evaluation area enable signal H region is shifted within the focusing evaluation area FEA so that position of the focal point detection pixel group FDA including three lines are moved from the position indicated by dotted lines to the position indicated by solid lines. S31 and S32 provide a processing section that shifts and sets positions of pixels in an image, for which contour component signals CES are outputted for determining a focusing state, based on the forceps position information.

In the case of NO in S31 and after S32, the CPU 39 supplies the focusing evaluation enable signals to the shape detection section 54 as focusing evaluation area instruction signals FEIS (S33).

Next, processing in the halation detection section 53, the shape detection section 54, the threshold value comparison section 55, the focal point switching instruction section 56 and the CPU I/F section 58 will be described.

Figure 21:
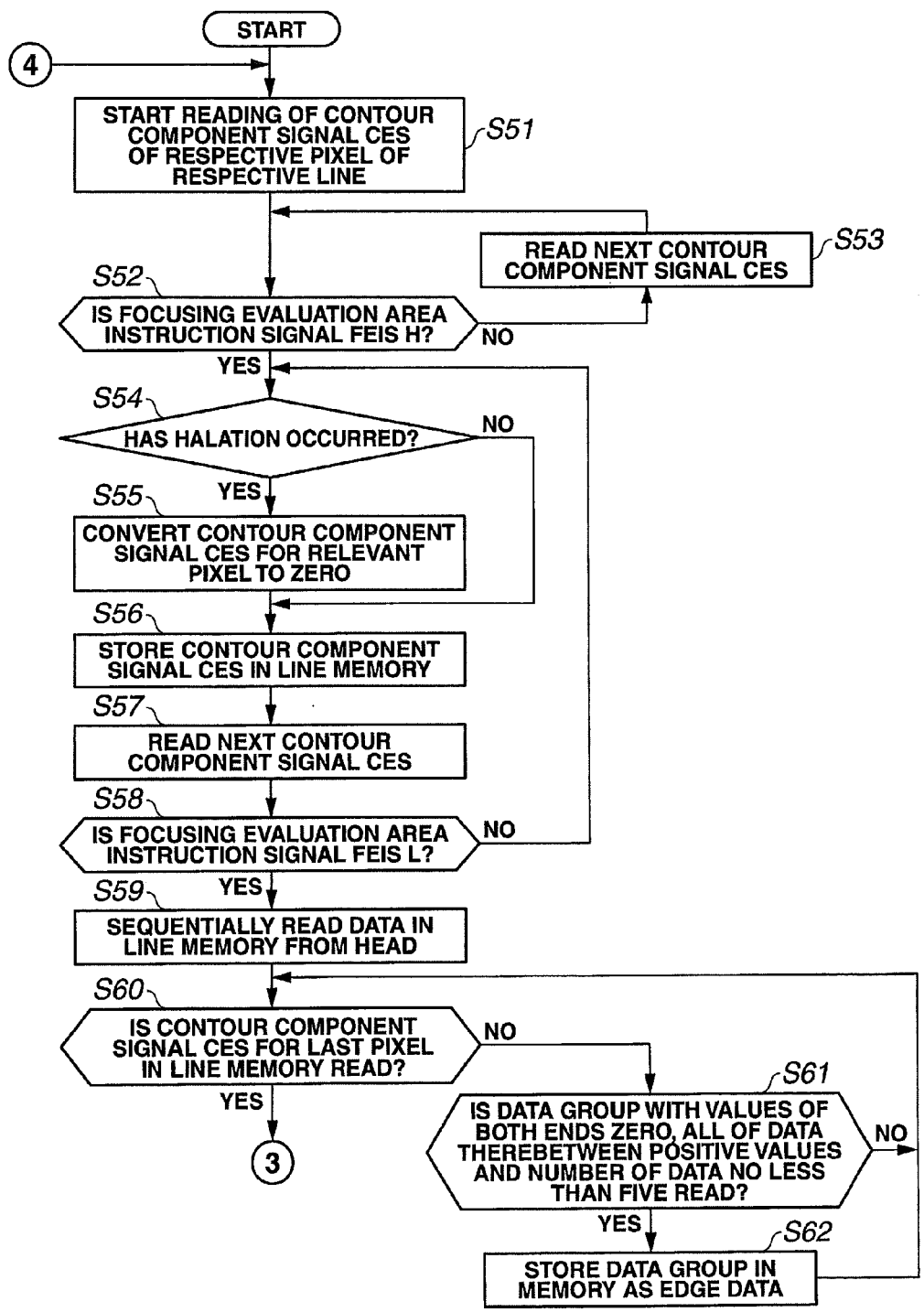
FIG. 21 is a flowchart illustrating an example of a flow of processing in a halation detection section 53, a shape detection section 54, a threshold value comparison section 55, a focal point switching instruction section 56 and a CPU I/F section 58, according to the embodiment of the present invention.

FIGS. 21 and 22 are flowcharts of the flow of processing in the halation detection section 53, the shape detection section 54, the threshold value comparison section 55, the focal point switching instruction section 56 and the CPU I/F section 58.

First, the CPU 39 start reading of a contour component signal CES in the image effective region VA from the contour enhancement circuit 36 (S51). The CPU 39 determines whether or not a focusing evaluation area instruction signal FEIS corresponding to a position of a pixel for the read contour component signal CES is H (S52).

If the focusing evaluation area instruction signal FEIS for the read contour component signal CES is not H (S52: NO), the CPU 39 reads a next contour component signal CES (S53) and proceeds the above-described processing in S52.

If the focusing evaluation area instruction signal FEIS for the read contour component signal CES is H (S52: YES), the CPU3 determines whether or not a halation has occurred in the position of the pixel for the read contour component signal CES (S54). This determination can be made based on a luminance signal BS from the contour enhancement circuit 36. Occurrence of a halation is determined based on whether or not the luminance signal BS is no less than a predetermined threshold value THh for determining occurrence or non-occurrence of a halation.

If a halation has occurred (S54: YES), the CPU 39 converts the contour component signal CES for the pixel to 0 (zero) (S55). In the case of NO in S54 and after S55, the CPU 39 stores the contour component signal CES in the line memory 44 (S56).

As described above, a distribution of signals included in signal contour component signals is determined except contour component signals CES for pixels whose detected luminance values are no less than the predetermined threshold value THh.

Then, the CPU 39 reads a next contour component signal CES (S57), and determines whether or not a focusing evaluation area instruction signal FEIS for the read signal is L (S58).

In the case of NO in S58, the focusing evaluation area instruction signal FEIS for the read signal is H, and thus, the processing returns to S54.

In the case of YES in S58, contour component signals CES for one line in the focal point detection pixel group FDA or FDA1 have been read. Accordingly, the CPU 39 reads the contour component signals CES stored in the line memory 44 from the head of the line memory 44 (S59).

The CPU 39 determines whether or not the contour component signal CES for the last pixel in the line memory 44 has been read (S60), and if the contour component signal CES for the last pixel has not been read (S60: NO), the CPU 39 determines whether or not a group of data with both ends zero, data therebetween all positive values and no less than a predetermined number (here, for example, five) of data included has been read (S61).

In the line memory 44, contour component signals CES for one line in a focal point detection pixel group FDA or FDA1 in a focusing evaluation area are stored. In the line, contour component signals CES for edge parts are stored. If the image is in focus, groups of contour component signals CES exhibiting the shape illustrated in FIG. 15 exist successively. If the image is out of focus, groups of contour component signals exhibiting the shape illustrated in FIG. 16 exist. In a region with no edge parts, no contour component signals CES appear. Accordingly, in S61, it is determined whether or not a group of data with both ends zero, data therebetween all positive values and no less than a predetermined number of data included has been read.

In the case of NO in S61, the processing returns to S60. In the case of YES in S61, the data group is stored in the memory 45 as edge data (S62), and the processing moves to S60.

The case of YES in S60 means that the contour component signal CES for one line in the focal point detection pixel group FDA or FDA1 in the focusing evaluation area has been read.

Next, the CPU 39 determines whether or not edge data for which shape determination has not been made exists in the memory 45 (S63). In the case of YES in S63, the CPU 39 reads edge data for which shape determination has not been made from the memory 45 (S64), and determines whether or not the edge data has only one inflection point, and the value of the contour component signal CES changes from an increase to a decrease along the X direction (S65).

In the case of YES in S65, that is, if the edge data exhibits a change as illustrated in FIG. 15, the CPU 39 determines that the edge data is an in-focus edge group (S66), and stores a maximum (MAX) value of the in-focus edge group in the memory 45 (S67). As described above, in S65, whether or not a plurality of contour component signals CES for edge data exhibit a predetermined signal distribution as illustrated in FIG. 15, and if the contour component signals CES exhibits the predetermined signal distribution, the edge data is determined as an in-focus edge group.

In the case of NO in S65, that is, if the edge data does not have a change as illustrated in FIG. 15, the CPU 39 determines the edge data as an out-of-focus edge group (S68).

After S67 and S68, the processing returns to S63.

In the case of NO in S63, that is, if all of the edge data has been read and the above-described determination has been made therefor, whether or not the observation mode is a narrow-band imaging (NBI) mode is determined (S69). In the case of YES in S69, the CPU 39 deletes all of in-focus edge groups each having a maximum value of no more than a predetermined threshold value α, which has been stored in S67, from the memory 45 (S70).

In the case of NO in S69 and after S70, the CPU 39 determines whether or not automatic gain control (AGC) is on (S71). In the case of YES in S71, the CPU 39 deletes all of in-focus edge groups each having a maximum value of no more than a predetermined threshold value β, which has been stored in S67, from the memory 45 (S72).

In the case of NO in S71 and after S72, the CPU 39 deletes all of in-focus edges having a maximum value of no more than γ, from the memory 45 (S73), and determines whether or not the set sensitivity is high (S74). Note that, here, a relationship among α, β and γ is α>β>γ. Each of S70, S72 and S73 provides a signal value comparison section that compares a maximum value of contour component signals CES and a predetermined threshold value. Accordingly, the predetermined threshold value varies depending on the observation mode, and also varies depending on whether the automatic gain control (AGC) is in an on state or an off state.

In the case of YES in S74, the CPU 39 determines whether or not the number of in-focus edge groups is no less than a predetermined number, here, no less than K (S75). In the case of YES in S75, the CPU 39 determines whether or not a movement of the object is no more than a predetermined value (S76). Whether or not a movement of the object is a movement of no less than the predetermined threshold value related to movement is determined based on the variation information from the frame comparison circuit 41.

In the case of YES in S76, that is, if a movement of the object is no more than the predetermined value, the CPU 39 determines that the line is in focus (S77).

In the case of NO in S75 and in the case of NO in S76, the CPU 39 determines that the line is out of focus (S78).

In the case of NO in S74, that is, if the sensitivity is low, the CPU determines whether or not the number of in-focus edge groups is no less than a predetermined number, here, no less than L (S79). Here, L>K. Where a high sensitivity has been set, if the number of in-focus edge groups is no less than K (for example, three), the line is determined as being in focus; however, where a high sensitivity has not been set, the line is not determined as being in focus unless the number of in-focus edge groups is no less than L (for example, five) (S79: NO). As described above, a focusing state of each line is determined based on the number of predetermined distributions of a plurality of contour component signals CES exhibiting the predetermined distribution in each line.

After the determinations in S77 and S78, the CPU 39 determines whether or not the above-described processing has ended for each of a predetermined number of lines (S80). In S80, in the present embodiment, the focusing evaluation area FEA includes the focal point detection pixel group FDA or FDA1 including three lines, and thus, whether or not the above-described processing has ended for all of the three lines.

In the case of NO in S80, the processing moves to S51. In other words, in the present embodiment, a focal point detection pixel group FDA or FDA1 includes three lines, and the above-described processing has not been performed for all of the three lines, and thus, the above-described processing is performed for the remaining two lines.

Also, in the case of YES in S80, the above-described processing has ended for the predetermined number of lines, and thus, the CPU 39 determines whether or not the entire screen is in focus (S81).

If the entire screen is in focus, the processing ends, and if the entire screen is not in focus, the CPU 39 outputs a focal point switching instruction signal to the actuator drive section 42 (S82).

Whether or not the entire screen is in focus is determined from results of determinations for the respective lines: for example, if no less than two lines from among the three lines are determined as being in focus, the entire screen is determined as being in focus and if no more than one line from among the three lines is determined as being in focus, the entire screen is determined as being out of focus.

As described above, in the present embodiment described above, a focusing state is evaluated and determined according to whether or not a signal distribution of contour component signals CES is a predetermined distribution, and movement of the moving lens is controlled based on a result of comparison between a maximum value of the contour component signals CES and a predetermined threshold value.

Accordingly, while conventionally, focusing evaluation is performed by mere level comparison between contour enhancement signals obtained by contour enhancement processing and a predetermined threshold value and focusing evaluation differs between an image having large luminance values in its entirety and an image having small luminance values in its entirety, resulting in a decrease in precision of focusing evaluation, in the present embodiment described above, determination of a signal distribution of contour component signals CES is made, a focusing state is evaluated based on results of comparison between signal levels of the contour component signals CES and a predetermined threshold value, to perform focusing control, enabling enhancement of precision of focusing evaluation in the endoscope apparatus.

As described above, the above-described embodiment enables provision of an endoscope apparatus capable of performing high-precision focusing evaluation using contour component signals.

The present invention is not limited to the above-described embodiment and various modifications and alternations or the like are possible without departing from the spirit of the present invention.

What is claimed is:

1. An endoscope apparatus having a plurality of observation modes, the endoscope apparatus comprising:
   an objective optical system including a moving lens;
   an image pickup section that picks up an image of an object via the objective optical system;
   a contour enhancement section that performs contour enhancement of an image outputted from the image pickup section and outputs contour component signals;
   a signal value comparison section that compares a maximum value of the contour component signals and a predetermined threshold value according to the observation mode;
   a focusing state determination section that determines a focusing state by determining a signal distribution of the contour component signals; and
   a drive control section that controls movement of the moving lens based on the focusing state determined by the focusing state determination section and a result of the comparison by the signal value comparison section.

2. The endoscope apparatus according to claim 1, further comprising an automatic gain control circuit that controls a gain of an image signal outputted from the image pickup section,
   wherein the signal value comparison section determines the predetermined threshold value based on the gain of the automatic gain control circuit, and performs the comparison based on the determined threshold value.

3. The endoscope apparatus according to claim 2,
   wherein each of the contour component signals includes an edge component signal for a respective pixel, the edge component signal being obtained by calculation from a pixel value of a pixel of interest and pixel values of a plurality of pixels in a periphery of the pixel of interest in the image; and
   wherein the focusing state determination section determines that the image is in focus if a plurality of contour component signals generated by calculation while the pixel of interest is shifted from one to another by one pixel in a predetermined direction in the image exhibit a predetermined distribution.

4. The endoscope apparatus according to claim 3,
   wherein the image outputted from the image pickup section includes a focal point detection pixel group including a plurality of lines; and
   wherein the focusing state determination section determines the focusing state based on a number of the predetermined distributions of the plurality of contour component signals exhibiting the predetermined distribution in each of the lines.

5. The endoscope apparatus according to claim 4,
   wherein when the plurality of contour component signals are generated one by one for the respective pixels in the predetermined direction and outputted, the predetermined distribution includes a plurality of signal parts in a monotonic increase and a plurality of signal parts in a monotonic decrease following the plurality of signal parts in a monotonic increase; and
   wherein one plurality of signal parts in a monotonic increase and one plurality of signal parts in a monotonic decrease are included in the predetermined distribution.

6. The endoscope apparatus according to claim 4, comprising a forceps position detection section that detects a position of a forceps in the image picked up by the image pickup section,
   wherein the focusing state determination section sets positions of pixels in the image for which the contour component signals for determining the focusing state are outputted, based on forceps position information from the forceps position detection section.

7. The endoscope apparatus according to claim 5, comprising
   a luminance value detection section that detects a luminance value of each pixel in the image; and
   a lumen detection section that detects a lumen from the luminance values detected by the luminance value detection section,
   wherein the focusing state determination section sets a focusing determination area in the image for determining the focusing state, based on information on a position of the lumen detected by the lumen detection section.

8. The endoscope apparatus according to claim 7, wherein the focusing state determination section divides the image into a plurality of areas, and sets an area other than an area determined to include the lumen based on the information on the position of the lumen from among the plurality of areas, as the focusing determination area.

9. The endoscope apparatus according to claim 8, comprising a luminance value detection section that detects a luminance value of each pixel in the image,
wherein the focusing state determination section determines the signal distribution included in the contour component signals except a contour component signal for a pixel having a luminance value of no less than a predetermined threshold value, the luminance value being detected by the luminance value detection section.

10. The endoscope apparatus according to claim 9, comprising:
a distance estimation section that estimates a distance to the object;
an electronic shutter state detection section that detects a state of an electronic shutter in the image pickup section; and
a diaphragm value detection section that detects a diaphragm value for adjusting a light amount of illuminating light from a light source apparatus,
wherein the distance estimation section estimates the distance to the object based on at least one of the state of the electronic shutter and the diaphragm value.

11. The endoscope apparatus according to claim 10, comprising a movement detection section that detects a movement of the object in the image,
wherein the focusing state determination section determines the signal distribution of the contour component signals, based on the detected movement of the object.

12. The endoscope apparatus according to claim 11, wherein the focusing state determination section does not determine the signal distribution of the contour component signals when the detected movement of the object has no less than a predetermined movement threshold value.

* * * * *